United States Patent

Bedoya Zurita et al.

[11] Patent Number: 5,869,518
[45] Date of Patent: Feb. 9, 1999

[54] AZACYCLOALKANE DERIVATIVES, THEIR PREPARATION AND THEIR APPLICATION IN THERAPY

[75] Inventors: Manuel Bedoya Zurita; Juan Antonio Diaz Martin; Gregorio del Sol Moreno; Ulpiano Martin Escudero Perez; Maria Dolores Jimenez Bargueno; Magali Romanach Ferrer, all of Madrid, Spain

[73] Assignee: SYNTHELABO, Le Plessis Robinson, France

[21] Appl. No.: 945,576

[22] PCT Filed: Apr. 12, 1996

[86] PCT No.: PCT/FR96/00555

§ 371 Date: Oct. 31, 1997

§ 102(e) Date: Oct. 31, 1997

[87] PCT Pub. No.: WO96/34870

PCT Pub. Date: Nov. 7, 1996

[30] Foreign Application Priority Data

May 3, 1997 [FR] France .................. 95 05260

[51] Int. Cl.⁶ ............. A61K 31/415; C07D 495/04
[52] U.S. Cl. ........... 514/412; 514/419; 548/453; 548/500
[58] Field of Search .................. 548/453, 500; 514/412, 419

[56] References Cited

U.S. PATENT DOCUMENTS

| 3,190,950 | 6/1965 | Miller ................ 548/453 X |
| 3,706,810 | 12/1972 | Brabander et al. ........ 548/453 X |
| 4,414,225 | 11/1983 | Sauter et al. .............. 424/274 |
| 4,608,384 | 8/1986 | Wierzbicki et al. ........ 514/413 |
| 5,190,938 | 3/1993 | Badore et al. ............ 514/215 |
| 5,380,742 | 1/1995 | Sevrin et al. ............. 514/397 |

FOREIGN PATENT DOCUMENTS

| 0180500 | 5/1986 | European Pat. Off. . |
| 0421861 | 4/1991 | European Pat. Off. . |
| 0514275 | 11/1992 | European Pat. Off. ........ 548/483 |
| 0599697 | 6/1994 | European Pat. Off. . |
| 0682028 | 11/1995 | European Pat. Off. . |

Primary Examiner—Floyd D. Higel
Attorney, Agent, or Firm—Jacobson, Price, Holman & Stern, PLLC

[57] ABSTRACT

Azacyloalkane derivatives of general formula

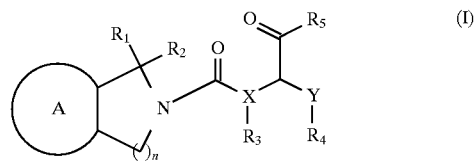

in which:

$R_1$ and $R_2$ represent a hydrogen atom, an alkyl group or a phenyl group, or $R_1$ and $R_2$ together form an oxo group, $R_3$ represents a hydrogen atom or an alkyl group, or alternatively $R_3$ forms a methylene group, $R_4$ represents an aromatic group or, when $R_3$ forms a methylene group, $R_4$ represents a phenylene group in which one carbon atom is linked to Y and another carbon atom, adjacent to the preceding one, is linked to the said methylene group, $R_5$ is either a group $OR_7$, where $R_7$ is a hydrogen atom or a benzyl group, or an $N^4$-methylpiperazinyl group, or alternatively a group $NHR_8$ where $R_8$ is a hydroxyl, pyridylmethyl or phenylmethyl group, A is an optionally substituted aromatic ring, n is equal to 1 or 2, X is CH, O or N, and Y is $CH_2$, O or S, the process for preparing them and their applications in therapy.

22 Claims, No Drawings

AZACYCLOALKANE DERIVATIVES, THEIR PREPARATION AND THEIR APPLICATION IN THERAPY

This application is a 371 of PCT/FR96/00555, filed Apr. 12, 1996.

The subject of the present invention is azacyloalkane derivatives, their preparation and their applications in therapy, especially in the treatment of diabetes, of obesity and of hyperglycaemia.

The azacyloalkane derivatives of the invention correspond to the general formula (I)

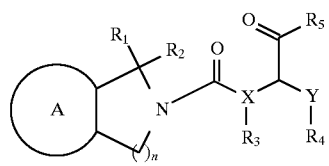

in which:
* $R_1$ and $R_2$, which are identical or different, each represent a hydrogen atom, a linear, branched or cyclic alkyl group comprising from 1 to 6 carbon atoms, or a phyenyl group optionally substituted with a linear or branched alkyl group comprising from 1 to 6 carbon atoms, with one or two halogen atoms or with a group $COOR_6$, $R_6$ being a hydrogen atom or a linear or branched alkyl group comprising from 1 to 6 carbon atoms, or $R_1$ and $R_2$ together form an oxo group,
* $R_3$ represents a hydrogen atom or a linear or branched alkyl group comprising from 1 to 4 carbon atoms, or alternatively $R_3$ forms a methylene group,
* $R_4$ represents an aromatic group chosen from a phenyl, naphthyl or pyridyl group, optionally substituted with a linear or branched alkyl group comprising from 1 to 6 carbon atoms, with one or two halogen atoms, with a nitro group, or with a group $COOR_6$, $R_6$ being as defined above,
or, when $r_3$ forms a methylene group, then $R_4$ represents a phenylene group in which one carbon atom is linked to Y and another carbon atom, adjacent to the preceding one, is linked to the said methylene group,
* $R_5$ is either a group $OR_7$, where $r_7$ is a hydrogen atom or a benzyl group, or an $N^4$-methylpiperazinyl, or alternatively a group $NHR_8$ where $R_8$ is a hydroxyl, pyridylmethyl or phenylmethyl group,
* n is equal to 1 or 2,
* A is an aromatic ring, optionally substituted with one or two halogen atoms, one or two linear or branched alkyl groups comprising from 1 to 4 carbon atoms, with a nitro group, with a group $COOR_6$, $R_6$ being as defined above, with one or two linear or branched alkoxy groups comprising from 1 to 6 carbon atoms or with a methylenedioxy group,
* X is CH, O or N, and
* Y is $CH_2$, O or S.

The compounds of formula (I) form, with pharmaceutically acceptable acids and bases, salts which are part of the invention. According to the present invention, the preferred salts are the sodium and calcium salts, which are such that $R_7$ represents a sodium or calcium atom.

The compounds of formula (I) comprise an asymmetric carbon atom. They can therefore exist in the form of enantiomers. These enantiomers, as well as mixtures thereof, including the racemic mixtures, are part of the invention.

Within the framework of the present invention, the terms below have the following meanings:

* an oxo group represents a group =O.
* an aromatic group consists of an unsaturated ring comprising from 3 to 14 carbon atoms, as well as, optionally, a heteroatom chosen from the group consisting of sulphur, oxygen and nitrogen, the said ring having a maximum number of unsaturations, taking into account optional substituents thereof.

Moreover, it may be noted that when n is equal to 1 or 2, this means that the number of carbon atoms included in the brackets is equal to 1 or 2. When n is equal to 1, the azacycloalkane derivative according to the invention is a dihydro-1H-pyrrole derivative. When n is equal to 2, the azacycloalkane derivative according to the invention is a tetrahydropyridine derivative.

According to a preferred embodiment of the invention, A is chosen from the group consisting of thiophene, benzene, furan and naphthalene, these aromatic groups being substituted or unsubstituted as indicated above. According to another advantageous feature of the invention, n is equal to 1 or $R_5$ is a hydroxyl group. Moreover, $r_4$ is preferably an unsubstituted phenyl group. As subgroup of compounds according to the invention, there may be mentioned especially that consisting of the derivatives of γ-oxo-α-(phenylmethyl)-5,6-dihydro-4H-thieno[3,4-c]pyrrole-5-butanoic acid of formula II

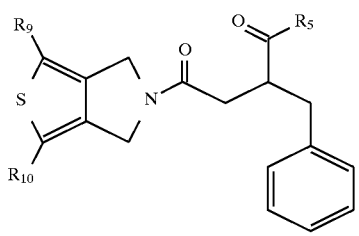

in which $R_5$ is as defined for the formula (I) and $R_9$ and $R_{10}$, which are identical or different, represent a hydrogen atom, a halogen atom or a linear or branched alkyl group comprising from 1 to 4 carbon atoms. The pure enantiomers, the mixtures of enantiomers, including the racemic mixtures, as well as the pharmaceutically acceptable salts of the compounds of formula (II), are part of the invention.

The compounds of formula (I) can be prepared according to the process represented in Scheme 1 of Annex 1. According to this process, a compound of formula (III)

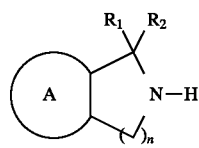

in which $R_1$, $R_2$, A and n are defined as in the formula (I), is reacted with a compound of general formula (IV)

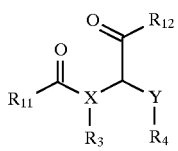

in which $R_3$, $R_4$, X and Y are defined as in the formula (I), $R_{11}$ represents a halogen atom or a hydroxyl group and $R_{12}$ is a linear or branched alkoxy group comprising from 1 to 4 carbon atoms, or a phenylalkoxy group in which the alkoxy part comprises from 1 to 4 carbon atoms, such as the benzyloxy group.

This reaction can be carried out in a solvent such as dichloromethane, in the presence of triethylamine and/or an agent for activating the acidic functional group such as isobutyl chloroformate or carbonyldiimidazole (CDI). Compounds of formula (Ia) are thus prepared in which $R_1$, $R_2$, $R_3$, $R_4$, $R_{12}$, A, n, X and Y have the means mentioned above. The compounds of formula (I) for which $R_5$ is a benzyloxy group can thus be directly obtained by choosing $R_{12}$ as being a benzyloxy group.

The compounds of the invention of formula (Ib), for which $R_5$ is a hydroxyl group, can be obtained by hydrogenolysis or hydrolysis of the compounds of formula (Ia) by means, for example, of sodium hydroxide or hydrochloric acid.

The compounds of the invention of formula (I) where $R_5$ is either an $N^4$-methylpiperazinyl group, or a group $NHR_8$ where $r_8$ is a hydroxyl, pyridylmethyl or phenylmethyl group, can be prepared by reacting the compounds of formula (Ia) with an amine of formula HZ in which Z represents an $N^4$-methylpiperazinyl group or a group $NHR_8$ as defined above, in the presence of carbonyl diimidazole.

The compounds of formula (III) can be prepared according to processes well known to persons skilled in the art, especially according to the processes described in French Patent Application No. 93 07538, or according to processes described in the literature, such as for example in Tetrahedron Letters, 36, 5877–5880 (1995).

More particularly, the compounds of formula (III), in which A is an optionally substituted benzene group, n is equal to 1, $R_1$ and $R_2$ each represent a hydrogen atom, can especially be prepared according to the two processes represented in schemes 2 and 3 of Annex 2.

According to the process of scheme 2, a compound of formula (V) in which $R_{13}$ represents a halogen atom, an $NO_2$ group, a linear or branched alkyl, comprising from 1 to 4 carbon atoms, is reacted with urea in order to prepare an imide compound of formula (VI) where $r_{13}$ has the meaning indicated above. The imide functional group of the compound of formula (VI) is then reduced with the aid of sodium borohydride, in the presence of boron trifluoroetherate, in order to obtain the compounds of formula (IIIa) where $R_{13}$ has the meaning indicated above.

According to scheme 3, a compound of formula (VII), in which $R_{14}$ represents a halogen atom, is reacted successively with a strong base such as n-butyllithium in a solvent such as tetrahydrofuran, then with N,N-dimethylformaide, then with sodium borohydride, and then finally with hydrochloric acid in order to obtain a compound of formula (VIII). The latter is subjected to the action of sodium hydride, and then to that of potassium tert-butoxide in the presence of water in order to obtain the compounds of formula (IIb) where $r_{14}$ represents a halogen atom.

The compounds of formula (IV) can be prepared according to processes described in the literature, such as for example in J. Am. Chem. Soc., 90, 3495–3502 (1968) or in J. Med. Chem., 36, 2788–2797 (1993).

The following examples illustrate the invention.

Analyses confirm the structure of the compounds.

EXAMPLE 1

γ-oxo-α(R,S)-(phenylmethyl)-5,6-dihydro-4H-furo[3,4-c] pyrrole-5-butanoic acid 1.1.—3,4-furandimethanol.

A solution of 7.2 g (39 mmol) of diethyl 3,4-furandicarboxylate in 95 ml of tetrahydrofuran is added, at 0° C., to 95 ml (95 mmol) of a 1M solution of lithium aluminium hydride in tetrahydrofuran. The solution is stirred at room temperature for 16 h and then 3.8 ml of water and 3.8 ml of a 15% sodium hydroxide solution is added at 0° C. The precipitate formed is filtered, washed with three times 100 ml of tetrahydrofuran, and then the pooled organic phases are washed with brine, dried over sodium sulphate, filtered and evaporated to dryness. 4.26 g of an oily product are obtained. Yield 85%.

1.2.—3,4-bis(chloromethyl)furan

A solution of 7.5 ml (105.3 mmol) of thionyl chloride in 30 ml of chloroform is added, at 0° C. to a solution of 5.3 g (41.36 mmol) of 3,4-furandimethanol in 30 ml of chloroform. The solution is stirred for 2 h at room temperature and then the mixture is poured into 100 ml of ice-cold water. The organic phase is decanted off, washed with twice 50 ml of cold water, dried over sodium sulphate and then evaporated to dryness. 3.97 g of an oily product are obtained. Yield 58%.

1.3.—5-Benzoyl-5,6-dihydro-4H-furo[3,4-c]pyrrole.

0.72 g (18 mmol) of a dispersion of sodium hydride in oil is added, at 0° C., to a solution of 0.75 g (6 mmol) of benzamide in 20 ml of N,N-dimethylformamide; the solution is stirred at room temperature for 90 min, then a solution of 1 g (6 mmol) of 3,4-bis(chloromethyl)furan in 20 ml of N,N-dimethylformamide is added. The solution is stirred for 2.5 h, cooled to 0° C., and 50 ml of water are added and the solution is extracted with three times 50 ml of ethyl acetate; the pooled organic phases are washed with brine, dried over sodium sulphate and then evaporated to dryness. The residue is purified by silica gel chromatography with the aid of the eluent mixture ethyl acetate/hexane ¼. 0.42 g of a white solid is obtained. Yield 32%.

Melting point: 84.5°–85.5° C.

1.4.—5,6-Dihydro-4H-furo[3,4-c]pyrrole.

30 ml (67.5 mmol) of a 2.5M aqueous solution of sodium hydroxide are added to a solution of 2.7 g (12.6 mmol) of 5-benzoyl-5,6-dihydro-4H-furo[3,4-c]pyrrole in 20 ml of ethanol. The mixture is stirred under reflux for 6.5 h; the ethanol is distilled off and then the solution is extracted with three times 30 ml of dichloromethane. The pooled organic phases are washed with brine, dried over sodium sulphate and evaporated to dryness. 1.25 g of an oily product are obtained, which product is used as it is for the next reaction.

1.5.—Phenylmethyl γ-oxo-α(R,S)-(phenylmethyl)-5,6-dihydro-4H-furo[3,4-c]pyrrole-5-butanoate.

1.48 g (9 mmol) of carbonyldiimidazole are added, at 0° C., to a solution of 2.5 g (8.3 mmol) of phenylmethyl 3-carboxy-2(R,S)-(phenylmethyl)-1-propanoate in 40 ml of tetrahydrofuran; the solution is stirred for 90 min. at room temperature and then a solution of 1 g (9 mmol) of 5,6-dihydro-4H-furo[3,4-c]pyrrole in 40 ml of tetrahydrofuran is added; after 2 h, the mixture is poured into ice-cold water and stirred for 30 min. The precipitate formed is filtered, it is washed with twice 20 ml of water and dried under vacuum. 2.85 g of a white solid are obtained. Yield 88%.

Melting point: 101°–102° C.

1.6.—γ-Oxo-α(R,S)-(phenylmethyl)-5,6-dihydro-4H-furo [3,4-c]pyrrole-5-butanoic acid.

10 ml of ethanol are added to a solution of 1 g (2.56 mmol) of phenylmethyl γ-oxo-α(R,S)-(phenylmethyl)-5,6-dihydro-4H-furo[3,4-c]pyrrole-5-butanoate in 10 ml of tetrahydrofuran followed, at 0° C., by a solution of 0.308 g (7.7 mmol) of sodium hydroxide in 10 ml of water. The mixture is stirred for 2 h at 0° C., and then for 2 h at room temperature. The solution obtained is concentrated, 30 ml of water are added and the solution is washed with twice 35 ml of diethyl ether. The aqueous phase is cooled, and then a 2M solution of hydrochloric acid is added to pH 2. The precipitate formed is filtered, it is washed with twice 20 ml of water and it is dried under vacuum. 0.47 g of a white solid is obtained. Yield 61%.

Melting point: 135°–137° C.

EXAMPLE 2

5-fluoro-γ-oxo-α(S)-(phenylmethyl)-2,3-dihydro-1H-isoindole-2-butanoic acid.

2.1.—N-[(4-Fluoro-2-formylphenyl)methyl]-2,2-dimethylpropanamide.

22.9 ml (57.3 mmol) of a 2.5M solution of n-butyllithium in hexane are added, at −78° C., to a solution of 5 g (23.9 mmol) of N-[(4-fluoro-phenyl)methyl]-2,2-dimethylpropanamide in 60 ml of tetrahydrofuran. The solution is stirred for 1 h at 0° C., cooled to −78° C. and then 2 ml of N,N-dimethylformamide are added and the solution is stirred for 2 h at 0° C. 20 ml of a saturated ammonium chloride solution are added, the solution is stirred for 30 min at room temperature and then 50 ml of water and 100 ml of ethyl acetate are added. The organic phase is washed with brine, it is dried over sodium sulphate and then it is evaporated to dryness. The residue crystallizes from an ethyl acetate/hexane mixture. 3 g of a white solid are obtained. Yield 53%.

Melting point: 62°–64° C.

2.2.—N-[[4-Fluoro-2-(hydroxymethyl)phenyl]methyl]-2,2-dimethylpropanamide.

0.08 g (2.1 mmol) of sodium borohydride is added, at 0° C., to a solution of 0.5 g (2.1 mmol) of N-[(4-fluoro-2-formylphenyl)methyl]-2,2-dimethylpropanamide in 15 ml of methanol. The solution is stirred for 4 h at room temperature, and then the solvent is removed. 20 ml of a saturated sodium hydrogen carbonate solution are added and the solution is extracted with twice 30 ml of dichloromethane. The pooled organic phases are washed with brine, they are dried over sodium sulphate and then they are evaporated to dryness. The product crystallizes from an ethyl acetate/hexane mixture in the form of a white solid. 0.27 g is obtained. Yield 54%.

Melting point: 102°–103° C.

2.3.—N-[[2-Chloromethyl)-4-fluorophenyl]methyl]-2,2-dimethylpropanamide.

A mixture of 2.77 g (11.57 mmol) of N-[[4-fluoro-2-(hydroxymethyl)phenyl]methyl]-2,2-dimethylpropanamide and 20 ml of concentrated hydrochloric acid is heated at 60° C. for 20 h; the solvent is removed and 3 g of a white solid are obtained. Quantitative yield.

Melting point: 99°–103° C.

2.4.—2-(2,2-dimethyl-1-oxopropyl)-5-fluoro-2,3-dihydro-1H-isoindole.

0.49 g (12.3 mmol) of a dispersion of sodium hydride at 60% in oil is added, at 0° C., to a solution of 2.9 g (11.25 mmol) of N-[[2-chloromethyl)-4-fluorophenyl]methyl]-2,2-dimethylpropanamide in 70 ml of N,N-dimethylformamide. The solution is stirred at 0° C. for 1 h, and then 2 ml of 6N hydrochloric acid are added. The solvent is removed and the residue is purified by chromatography on a silica gel column with the aid of the eluent mixture ethyl acetate/hexane ⅕. 2.1 g of a white solid are obtained. Yield 85%.

Melting point: 80°–82° C.

2.5.—5-Fluro-2,3-dihydro-1H-isoindole.

0.3 ml (16.7 mmol) of water is added to a suspension of 6.6 g (54 mmol) of potassium tert-butoxide in 140 ml of tetrahydrofuran; the mixture is stirred for 5 min, and then 1.8 g (8.13 mmol) of 2-(2,2-dimethyl-1-oxopropyl)-5-fluoro-2,3-dihydro-1H-isoindole are added. The mixture is stirred at 70° C. for 48 h, it is filtered on celite, washed with twice 50 ml of tetrahydrofuran and then the filtrates are evaporated to dryness. 20 ml of 6N hydrochloric acid are added and the solution obtained is washed with twice 20 ml of ethyl acetate, and then the aqueous phase is alkalinized with 6N sodium hydroxide to pH 14 and it is extracted with three times 30 ml of ethyl acetate. The pooled organic phases are washed with brine, they are dried over sodium sulphate and they are evaporated to dryness. 0.69 g of an oily product is obtained.

Yield 61%.

2.6.—Phenylmethyl 5-fluoro-γ-oxo-α(S)-(phenylmethyl)-2,3-dihydro-1H-isoindole-2-butanoate.

This compound was obtained in the form of an oil, according to the process described in stage 1.5 of Example 1, from phenylmethyl 3-carboxy-2(S)-(phenylmethyl)-1-propanoate and 5-fluoro-2,3-dihydro-1H-isoindole.

2.7.—5-Fluro-γ-oxo-α(S)-(phenylmethyl)-2,3-dihydro-1H-isoindole-2-butanoic acid.

150 mg of 10% palladized carbon are added to a solution of 1.18 g (2.83 mmol) of phenylmethyl 5-fluoro-γ-oxo-α(S)-(phenylmethyl)-2,3-dihydro-1H-isoindole-2-butanoate in 5 ml of ethyl acetate and the mixture is hydrogenated at the pressure of 20 psi (137,921 Pa) for 2.5 h. After filtration on celite and then evaporation of the solvent, the product is crystallized from diethyl ether. 0.6 g of a white solid is obtained. Yield 65%.

Melting point: 136°–138° C.

EXAMPLE 3

5-methyl-γ-oxo-α(S)-(phenylmethyl)-2,3-dihydro-1H-isoindole-2-butanoic acid.

3.1.—5-Methyl-1H-isoindole-1,3-(2H)-dione.

A mixture of 8.1 g (50 mmol) of 5-methylisobenzofuran-1,3-dione and 6 g (100 mmol) of urea is heated at 170° C. for 45 min. The molten mixture is poured over water, the precipitate formed is filtered, it is dissolved in 250 ml of dichloromethane and then the mixture is washed successively with a saturated sodium hydrogen carbonate solution, with water and with brine. Finally, it is dried over sodium sulphate and evaporated to dryness. 5.7 g of a slightly yellow solid is obtained. Yield 71%.

Melting point: 196°–197° C.

3.2.—5-Methyl-2,3-dihydro-1H-isoindole.

1.87 g (49.6 mmol) of sodium borohydride are added to a suspension of 2 g (12.4 mmol) of 5-methyl-1H-isoindole-1,3-(2H)-dione in 50 ml of tetrahydrofuran. The mixture is cooled to 0° C. and a solution of 6.25 ml (49.6 mmol) of boron triluoride etherate in 15 ml of tetrahydrofuran is added. The mixture is heated at reflux for 5 h, cooled, 25 ml of methanol are added, the mixture is stirred for 1 h at room temperature, and then 25 ml of 6N hydrochloric acid are added and the mixture is heated at reflux for 1 h. The mixture is filtered, the filtrate is concentrated, it is washed with twice 40 ml of diethyl ether and it is evaporated to dryness. 20 ml of a 5N sodium hydroxide solution are added and the mixture is extracted twice with 100 ml of dichloromethane. The organic phases are washed with brine, they are dried over sodium sulphate and then they are evaporated to dryness. 0.65 g of an oily product is obtained.

3.3.—Phenylmethyl 5-methyl-γ-oxo-α(S)-(phenylmethyl)-2,3-dihydro-1H-isoindole-2-butanoate.

This compound was obtained in the form of an oil, according to the process described in state 1.5 of Example 1, from phenylmethyl 3-carboxy-2(S)-(phenylmethyl)-1-propanoate and 5-methyl-2,3-dihydro-1H-isoindole.

3.4.—5-Methyl-γ-oxo-α(S)-(phenylmethyl)-2,3-dihydro-1H-isoindole-2-butanoic acid.

This compound was obtained in the form of an oil, according to the process described in stage 2.7 of Example 2, from phenylmethyl 5-methyl-γ-oxo-α(S)-(phenylmethyl)-2,3-dihydro-1H-isoindole-2-butanoate. The sodium salt of this compound has a melting point greater than 250° C.

By reproducing this example using as starting material 1H-isoindole-1,3-(2H)-dione, it was possible to prepare γ-oxo-α(S)-(phenylmethyl)-2,3-dihydro-1H-isoindole-2-butanoic acid, γ-oxo-α(R)-(phenylmethyl)-2,3-dihydro-1H-isoindole-2-butanoic acid and γ-oxo-α(R,S)-(phenylmethyl)-2,3-dihydro-1H-isoindole-2-butanoic acid.

EXAMPLE 4

α(R,S)-[[(2,3-dihydro-1H-isoindol-2-yl)carbonyl]amino]benzenepropanoic acid.

4.1.—Phenylmethyl α(R,S)-[[(2,3-dihydro-1H-isoindol-2-yl)carbonyl]amino]benzenepropanoate acid.

A solution of 1.09 g (4.26 mmol) of phenylmethyl α-aminobenzenepropanoate in 10 ml of tetrahydrofuran is added to a solution of 0.71 g (4.39 mmol) of carbonyldiimidazole in 10 ml of tetrahydrofuran. After 30 min, a solution of 0.45 g (3.76 mmol) of 2,3-dihydroisoindole in 5 ml of tetrahydrofuran is added and the solution is stirred for 16 h at 60° C. The solvent is removed, the residue is dissolved in 100 ml of dichloromethane and the solution is washed with 2N hydrochloric acid, dried over sodium sulphate and then evaporated to dryness. The residue is purified by chromatography on a silica gel column with the aid of the eluent mixture ethyl acetate/hexane; ¼. 1.25 g of an oily compound are obtained. Yield: 83%.

4.2.—α(R,S)-[[(2,3-dihydro-1H-isoindol-2-yl)carbonyl]amino]benzenepropanoic acid.

This compound was obtained in the form of a white solid, according to the process described in stage 2.7 of Example 2, from phenylmethyl α(R,S)-[[(2,3-dihydro-1H-isoindol-2-yl)carbonyl]amino]benzenepropanoate.

Melting point: 185°–187° C.

EXAMPLE 5 trans-3-[(2,3-Dihydro-1H-isoindol-2-yl)carbonyl]-1,2,3,4-tetrahydronaphthalene-2-carboxylic acid.

5.1.—Ethyl phenylmethyl trans-1,2,3.4-tetrahydronaphthalene-2,3-dicarboxylate.

A solution of 1.32 g (15 mmol) of ethyl phenylmethyl E-but-2-enedioate in 20 ml of tetrahydrofuran is added, over 1 h, to a suspension of 1.84 g (45 mmol) of chromium chloride in a mixture of 20 ml of tetrahydrofuran and 20 ml of hexamethylphosphoramide. The mixture is stirred for 48 h then it is poured into 100 ml of 1N hydrochloric acid and extracted with four times 50 ml of ethyl acetate. The pooled organic phases are washed successively with 100 ml of water, 100 ml of a 5N lithium chloride solution, 100 ml of water and finally with brine. The solution is dried over sodium sulphate, evaporated to dryness and the residue is chromatographed on a silica gel column with the aid of the eluent mixture ethyl acetate/hexane: ⅗. 0.91 g of an oily product is obtained. Yield: 47%.

5.2.—2-Ethyl trans-1,2,3,4-tetrahydronaphthalene-2,3-dicarboxylate.

A solution of 0.9 g (2.7 mmol) of ethyl phenylmethyl trans-1,2,3,4-tetrahydronaphthalene-2,3-dicarboxylate is hydrogenated in the presence of 0.4 g of 10% palladized carbon at a pressure of 20 psi (137,921 Pa) for 5 h. The mixture is filtered on celite and it is evaporated to dryness. 0.65 g of a white solid is obtained. Yield 97%.

Melting point: 100°–103° C.

5.2.—Ethyl trans-3-[(2,3-dihydro-1H-isoindol-2-yl)carbonyl]-1,2,3,4-tetrahydronaphthalene-2-carboxylate.

0.38 ml (5.2 mmol) of thionyl chloride is added, at 0° C., to a solution of 0.65 g (2.6 mmol) of 2-ethyl trans-1,2,3,4-tetrahydronaphthalene-2,3-dicarboxylate in 10 ml of dichloromethane. The solution is stirred at room temperature for 2 h and evaporated to dryness. The residue is dissolved in 10 ml of dichloromethane and the solution obtained is added to a solution of 0.31 g (2.6 mmol) of 2,3-dihydro-1H-isoindole in 10 ml of dichloromethane and 0.72 ml (5.2 mmol) of triethylamine, cooled to 0° C. The mixture is stirred for 4 h at room temperature, 10 ml of water are added, the organic phase is decanted off, washed with brine, dried over sodium sulphate and then evaporated to dryness. The residue is purified by silica gel chromatography with the aid of the eluent mixture ethyl acetate/hexane ¼. 0.55 g of a white solid is obtained. Yield 61%.

Melting point: 119°–121° C.

5.4.—trans-3-[(2,3-dihydro-1H-isoindol-2-yl)carbonyl]-1,2,3,4-tetrahydronaphthalene-2-carboxylic acid.

This compound is obtained in the form of a white solid, according to the process described in stage 1.6 of Example 1, from ethyl trans-3-[(2,3-dihydro-1H-isoindol-2-yl)carbonyl]-1,2,3,4-tetrahydronaphthalene-2-carboxylate.

Melting point: 224°–226° C. (this compound is listed in the table below, under No. 23).

EXAMPLE 6

Phenylmethyl γ-oxo-α-(phenylmethyl)-5,6-dihydro-4H-thieno[3,4-c]pyrrole-5-butanoate 6.1. Phenylmethyl 1,1-dimethylethyl 2-(phenylmethyl)-1,4-butanedioate.

5 ml (12 mmol) of a 2.5M solution of butyllithium in hexane are added, at −5° C., to a solution of 1.66 ml (12 mmol) of diisopropylamine in 15 ml of dry tetrahydrofuran. After 30 min at this temperature, the solution is cooled to −70° C. and then a solution of 2.40 g (10 mmol) of phenylmethyl 3-phenylpropionate in 15 ml of tetrahydrofuran is added. After 30 min, 2.26 ml (14 mmol) of 1,1-dimethylethyl bromoacetate are added and the mixture is stirred at 0° C. for 2 h and it is poured into 100 ml of a saturated ammonium chloride solution. The organic phase is decanted off, washed with a saturated sodium chloride solution, dried over sodium sulphate and then evaporated to dryness. The residue is chromatographed on a silica column with the aid of the eluent mixture ethyl acetate/hexane ¹⁄₁₀. 2 g of an oily product are obtained.

6.2. Phenylmethyl 3-carboxy-2-(phenylmethyl)-1-propanoate 8 ml of trifluoroacetic acid are added, at 0° C., to a solution of 2 g (5.6 mmol) of phenylmethyl 1,1-dimethylethyl 2-(phenylmethyl)-1,4-butanedioate in 16 ml of dichloromethane. After 7 h at room temperature, the mixture is evaporated to dryness and the residue is recrystallized from cyclohexane. 1.05 g of a white product are obtained.

Melting point: 86°–87° C.

6.3. Phenylmethyl γ-oxo-α-(phenylmethyl)-5,6-dihydro-4H-thieno[3,4-c]pyrrole-5-butanoate 0.49 ml (6.8 mmol) of thionyl chloride is added, at 0° C., to a solution of 1.01 g (3.4 mmol) of phenylmethyl 3-carboxy-2-(phenylmethyl)-1-propanoate in 15 ml of dichloromethane, followed by two drops of N,N-dimethylformamide. After 2 h at room temperature, the mixture is evaporated to dryness and the residue is dissolved in 25 ml of dichloromethane. The solution is cooled to 0° C. and then a solution of 0.81 g (3.4 mmol) of 5,6-dihydro-4H-thieno[3,4-c]pyrrole trifluoroacetate and 1.42 ml (10.2 mmol) of triethylamine in 25 ml of dichloromethane is added. After 16 h at room temperature, 25 ml of water are added, and the organic phase is decanted off, washed with a saturated sodium chloride solution and then dried over sodium sulphate and evaporated to dryness. The residue is chromatographed on a silica gel with the aid of the eluent mixture ethyl acetate/hexane ⅗. 0.52 g of a white solid is obtained.

Melting point: 122°–124° C.

EXAMPLE 7

γ-oxo-α-(phenylmethyl)-5,6-dihydro-4H-thieno[3,4-c]pyrrole-5-butanoic acid.

15 ml of ethanol are added to a solution of 1.22 g (3 mmol) of phenylmethyl γ-oxo-α-(phenylmethyl)-5,6-dihydro-4H-thieno[3,4-c]pyrrole-5-butanoate in 15 ml of tetrahydrofuran, followed, at 0° C., by a solution of 0.36 g (9 mmol) of sodium hydroxide. After 1 h at room temperature, the medium is concentrated to about 15 ml, 15 ml of water are added and then the mixture is acidfied with 2N hydrochloric acid to pH 2 and extracted with three times 25 ml of ethyl acetate. The organic phases are pooled, washed with a saturated sodium chloride solution, dried over sodium sulphate and evaporated to dryness. The residue is triturated with diethyl ether to give 0.71 g of a white solid.

Melting point: 161°–163° C.

EXAMPLE 8

5-[4-(4-methylpiperazin-1-yl)-1,4-dioxo-3-(phenylmethyl)butyl]-5,6-dihydro-4H-thieno[3,4-c]pyrrole 0.55 g (3.39 mmol) of carbonyldiimidazole is added to a solution of 1 g (3.17 mmol) of γ-oxo-α-(phenylmethyl)-5,6-dihydro-4H-thieno[3,4-c]pyrrole-5-butanoic acid in 15 ml of dry tetrahydrofuran. The solution is stirred at room temperature for 1 h and then 0.42 ml (3.8 mmol) of 4-methylpiperazine is added and the solution is stirred at room temperature for 20 h. The mixture is then evaporated to dryness, the residue is dissolved in 50 ml of dichloromethane, and then the solution obtained is washed successively with twice 50 ml of a saturated sodium hydrogen carbonate solution and 20 ml of a saturated sodium chloride solution, dried over sodium sulphate and then evaporated to dryness. After recrystallization from ethanol, 1 g of a white solid is obtained.

Melting point: 156°–158° C.

The compounds of the invention are collated in the following table with their physical characteristics. It was possible to prepare them according to the processes described above.

TABLE

| No. | A | R₁ | R₂ | R₃ | R₄ | R₅ | n | X | Y | m.p. (°C.) | Config. |
|---|---|---|---|---|---|---|---|---|---|---|---|
| 1 | 2,5-dimethyl-thiophene | H | H | H | phenyl | OH | 1 | CH | CH₂ | 219–229 | (S) |
| 2 | 2,5-dichloro-thiophene | H | H | H | phenyl | OH | 1 | CH | CH₂ | 208–210 | (R,S) |
| 3 | thiophene | H | H | H | pyridyl | OH | 1 | CH | CH₂ | 181–183 | (R,S) |
| 4 | thiophene | H | H | H | naphthyl | OH | 1 | CH | CH₂ | 176–177 (d) | (R,S) |
| 5 | thiophene | H | H | H | phenyl | O(Ca)₁/₂ | 2 | CH | CH₂ | 173–178 (d) | (S) |
| 6 | thiophene | H | H | H | phenyl | OH | 1 | CH | S | 182–184 (d) | (R,S) |

TABLE-continued

| No. | A | R$_1$ | R$_2$ | R$_3$ | R$_4$ | R$_5$ | n | X | Y | m.p. (°C.) | Config. |
|---|---|---|---|---|---|---|---|---|---|---|---|
| 7 | ⁓⁓–C=C(F)–S–CH= | H | H | H | phenyl | ONa | 1 | CH | CH$_2$ | 246–248 | (S) |
| 8 | ⁓⁓–C=C(CO$_2$H)–S–CH= | H | H | H | phenyl | OH | 1 | CH | CH$_2$ | 149–151 (d) | (S) |
| 9 | phenyl | H | H | H | phenyl | OH | 2 | CH | CH$_2$ | 128–130 | (R,S) |
| 10 | phenyl | H | H | H | phenyl | ONa | 2 | CH | CH$_2$ | >250 | (S) |
| 11 | phenyl | H | H | H | phenyl | OH | 1 | CH | CH$_2$ | 164–166 | (R,S) |
| 12 | phenyl | H | H | H | phenyl | OH | 1 | CH | CH$_2$ | 133–135 | (S) |
| 13 | phenyl | H | H | H | phenyl | ONa | 1 | CH | CH$_2$ | >250 | (S) |

TABLE-continued

| No. | A | R₁ | R₂ | R₃ | R₄ | R₅ | n | X | Y | m.p. (°C.) | Config. |
|---|---|---|---|---|---|---|---|---|---|---|---|
| 14 | phenyl | H | H | H | phenyl | OH | 1 | CH | CH₂ | 131–133 | (R) |
| 15 | 4,5-dimethoxyphenyl | 4-chlorophenyl | H | H | phenyl | OH | 2 | CH | CH₂ | 97–101 | (RS,SS) |
| 16 | phenyl | cyclohexyl | H | H | phenyl | OH | 2 | CH | CH₂ | 66–75 | (RS,SS) |
| 17 | 4,5-dimethoxyphenyl | H | H | H | phenyl | OH | 2 | CH | CH₂ | 157–159 | (RS,SS) |
| 18 | methylenedioxyphenyl | H | H | H | phenyl | OH | 2 | CH | CH₂ | 120–122 | (R,S) |

TABLE-continued

| No. | A | $R_1$ | $R_2$ | $R_3$ | $R_4$ | $R_5$ | n | X | Y | m.p. (°C.) | Config. |
|---|---|---|---|---|---|---|---|---|---|---|---|
| 19 | phenyl | Me | H | H | phenyl | OH | 2 | CH | $CH_2$ | 138–139 | (RS,SS) |
| 20 | phenyl | O | — | H | phenyl | OH | 1 | CH | $CH_2$ | 185–187 | (R,S) |
| 21 | phenyl | H | H | H | phenyl | OH | 1 | N | $CH_2$ | 185–187 (d) | (R,S) |
| 22 | phenyl | H | H | Me | phenyl | OH | 1 | N | $CH_2$ | 124–125 | (R,S) |
| 23 | phenyl | H | H | —CH2— | 2-substituted phenyl | OH | 1 | CH | $CH_2$ | 224–226 (d) | TRANS (R,S) |
| 24 | phenyl | H | H | —CH2— | 2-substituted phenyl | OH | 1 | CH | $CH_2$ | 207–209 (d) | CIS (R,S) |
| 25 | 2,4-disubstituted phenyl | H | H | H | phenyl | ONa | 1 | CH | $CH_2$ | >250 | (S) |

TABLE-continued

Structure:
$R_1$—C(—$R_2$)(—A(n))—N(H)—C(O)—X(—$R_3$)—C(O)—$R_5$ with Y—$R_4$ branch

| No. | A | $R_1$ | $R_2$ | $R_3$ | $R_4$ | $R_5$ | n | X | Y | m.p. (°C.) | Config. |
|---|---|---|---|---|---|---|---|---|---|---|---|
| 26 | naphthyl | H | H | H | phenyl | OH | 1 | CH | $CH_2$ | 180–181 (d) | (S) |
| 27 | 3-F-phenyl | H | H | H | phenyl | OH | 1 | CH | $CH_2$ | 141–142 (d) | (S) |
| 28 | 4-F-phenyl | H | H | H | phenyl | OH | 1 | CH | $CH_2$ | 136–138 | (S) |
| 29 | 4-Cl-phenyl | H | H | H | phenyl | ONa | 1 | CH | $CH_2$ | >250 | (S) |
| 30 | 3,4-diCl-phenyl | H | H | H | phenyl | OH | 1 | CH | $CH_2$ | 196 (d) | (S) |

TABLE-continued

| No. | A | R₁ | R₂ | R₃ | R₄ | R₅ | n | X | Y | m.p. (°C.) | Config. |
|---|---|---|---|---|---|---|---|---|---|---|---|
| 31 | 2-nitrophenyl | H | H | H | phenyl | OH | 1 | CH | CH₂ | 126–128 (d) | (S) |
| 32 | phenyl | H | H | H | 4-CO₂Me-phenyl | OH | 1 | CH | CH₂ | 184–186 (d) | (R,S) |
| 33 | furan-3,4-diyl | H | H | H | phenyl | OH | 1 | CH | CH₂ | 139–141 | (R,S) |
| 34 | furan-3,4-diyl | H | H | H | phenyl | ONa | 1 | CH | CH₂ | >250 | (S) |
| 35 | phenyl | H | H | H | phenyl | OH | 1 | CH | O | 162–164 | (R,S) |
| 36 | phenyl | H | H | H | phenyl | OH | 1 | O | CH2 | 124–126 (d) | (R,S) |

TABLE-continued

Structure:

R₁R₂(OC)N-CH(A)-(·)ₙ  attached to X(R₃)-CH-C(O)R₅ with Y-R₄

| No. | A | R₁ | R₂ | R₃ | R₄ | R₅ | n | X | Y | m.p. (°C.) | Config. |
|---|---|---|---|---|---|---|---|---|---|---|---|
| 37 | thiophene | H | H | H | phenyl | OH | 1 | CH | CH₂ | 161–163 | (R,S) |
| 38 | thiophene | H | H | H | phenyl | OH | 1 | CH | CH₂ | 117–119 | (S) |
| 39 | thiophene | H | H | H | phenyl | OH | 1 | CH | CH₂ | 116–118 | (R) |
| 40 | thiophene | H | H | H | phenyl | ONa | 1 | CH | CH₂ | >250 (d) | (S) |
| 41 | thiophene | H | H | H | phenyl | OCH₂-phenyl | 1 | CH | CH₂ | 122–124 | (R,S) |
| 42 | thiophene | H | H | H | phenyl | OCH₂-phenyl | 1 | CH | CH₂ | 138–140 | (S) |

TABLE-continued

| No. | A | $R_1$ | $R_2$ | $R_3$ | $R_4$ | $R_5$ | n | X | Y | m.p. (°C.) | Config. |
|---|---|---|---|---|---|---|---|---|---|---|---|
| 43 | thiophene | H | H | H | phenyl | OCH$_2$-phenyl | 1 | CH | CH$_2$ | 140-142 | (R) |
| 44 | Cl-thiophene | H | H | H | phenyl | OH | 1 | CH | CH$_2$ | 148-150 | (R,S) |
| 45 | Cl-thiophene | H | H | H | phenyl | OH | 1 | CH | CH$_2$ | 100-102 | (S) |
| 46 | Cl-thiophene | H | H | H | phenyl | OCH$_2$-phenyl | 1 | CH | CH$_2$ | 88-90 | (S) |
| 47 | Br,Br-thiophene | H | H | H | phenyl | OH | 1 | CH | CH$_2$ | 212-214 | (R,S) |
| 48 | Br,Br-thiophene | H | H | H | phenyl | OCH$_2$-phenyl | 1 | CH | CH$_2$ | 110-112 | (R,S) |

TABLE-continued

| No. | A | R₁ | R₂ | R₃ | R₄ | R₅ | n | X | Y | m.p. (°C.) | Config. |
|---|---|---|---|---|---|---|---|---|---|---|---|
| 49 | 3-C(CH₃)₃, 5-C(CH₃)₃ thiophene | H | H | H | phenyl | OH | 1 | CH | CH₂ | 135-137 | (R,S) |
| 50 | thiophene | H | H | H | phenyl | 4-methylpiperazin-1-yl | 1 | CH | CH₂ | 156-158 | (R,S) |
| 51 | thiophene | H | H | H | phenyl | (pyridin-3-ylmethyl)amino | 1 | CH | CH₂ | 158-160 | (R,S) |
| 52 | thiophene | H | H | H | phenyl | NHOH | 1 | CH | CH₂ | 176-177 | (R,S) |

In this table:
*d = decomposition
*the symbol "⌇" represents the position of a carbon/carbon bond.

The compounds of the invention were tested in various biological tests.

They were in particular subjected to a test of hypoglycaemic activity in rats. This test was carried out on rats starved for 20 h. The products to be tested are administered orally. Blood samples are collected from the tail 0.5, 1, 2, 3, 5 and 7 h after administration of the product, according to the method described by H. OHNOTO in The Journal of Pharmacology and Experimental Therapeutics, 269, No. 2, 489–495 (1994).

The compounds of the invention reduce the basal glycaemia by 30 to 40% at doses of between 1 and 10 mg/kg.

The results show that the compounds of the invention have "in vivo" hypoglycaemic properties. They can therefore be used as medicinal product in the treatment of hyperglycaemia, diabetes and obesity.

The compounds of the invention may be provided, in combination with any appropriate excipient, in any form or pharmaceutical composition suitable for administration via the oral or parenteral route, for example in the form of tablets, hard gelatine capsules, sugar-coated tablets, or oral or injectable solutions.

The compounds of the invention can be administered at daily doses of between about 5 and 100 mg in adults orally, or of between 1 and 100 mg parenterally.

Annex 1

Scheme 1

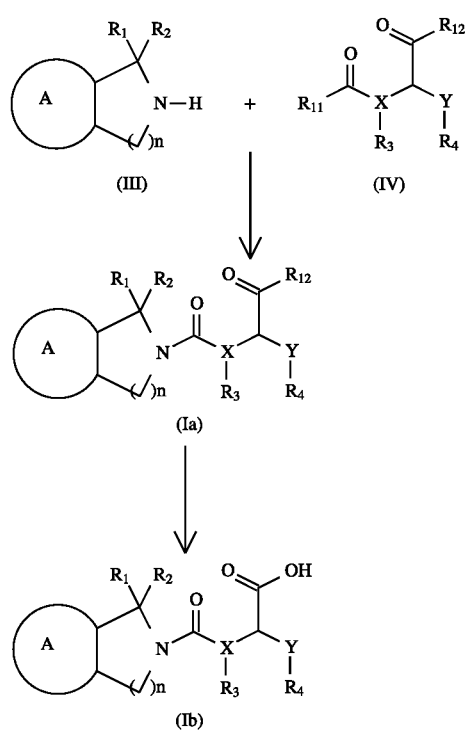

Annex 2

Scheme 2

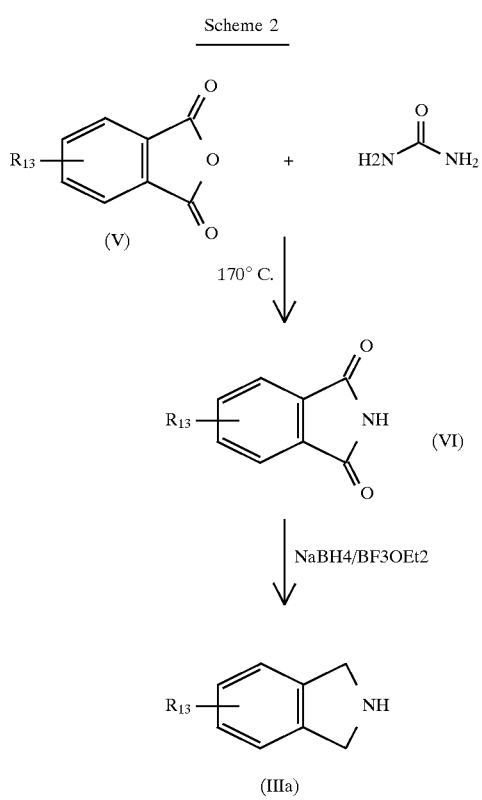

Scheme 3

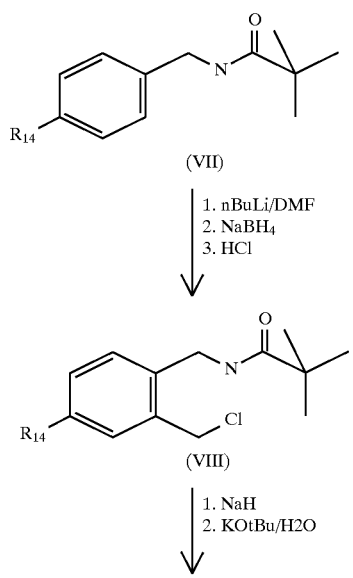

-continued
Scheme 3

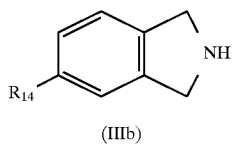

(IIIb)

We claim:
1. Azacycloalkane compound of formula (I)

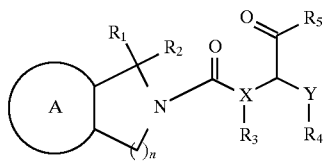

in which:
- $R_1$ and $R_2$, which are identical or different, each represent a hydrogen atom, a linear, branched or cyclic alkyl group having from 1 to 6 carbon atoms, or a phenyl group optionally substituted with a linear or branched alkyl group having from 1 to 6 carbon atoms, with one or two halogen atoms or with a group $COOR_6$, $R_6$ being a hydrogen atom or a linear or branched alkyl group having from 1 to 6 carbon atoms, or $R_1$ and $R_2$ together form an oxo group,
- $R_3$ represents a hydrogen atom, a linear or branched alkyl group having from 1 to 4 carbon atoms, or a methylene group,
- $R_4$ represents a phenyl, naphthyl or pyridyl group unsubstituted or substituted with a linear or branched alkyl group having from 1 to 6 carbon atoms, with one or two halogen atoms, with a nitro group, or with a group $COOR_6$, $R_6$ being as defined above, or, when $R_3$ forms a methylene group, then $R_4$ represents a phenylene group in which one carbon atom is linked to Y and another carbon atom, adjacent to the preceding one, is linked to the said methylene group,
- $R_5$ is either a group $OR_7$, where $R_7$ is a hydrogen atom or a benzyl group, or an $N_4$-methylpiperazinyl group, or a group $NHR_8$ where $R_8$ is a hydroxyl, pyridylmethyl or phenylmethyl group,
- n is equal to 1 or 2,
- A is a thiophene, benzene, furan or naphthalene ring unsubstituted or substituted with one or two halogen atoms, one or two lienar or branched alkyl groups having from 1 to 4 carbon atoms, with a nitro group, with a group $COOR_6$, $R_6$ being as defined above, with one or two linear or branched alkoxy groups having from 1 to 6 carbon atoms or with a methylenedioxy group,
- X is CH, O or N, and
- Y is $CH_2$, O or S, in the form of a pure enantiomer, a mixture of enantiomers, a racemic mixture or their addition salts with pharmaceutically acceptable acids or bases.

2. Compound according to claim 1, wherein A is a thiophene, furan or benzene ring unsubstituted or substituted with one or two halogen atoms, one or two linear or branched alkyl groups having from 1 to 4 carbon atoms, or a nitro group.

3. Compound according to claim 1 wherein n is equal to 1 and $R_5$ is a hydroxyl group.

4. Compound according to claim 1, wherein the compound is a compound of formula II

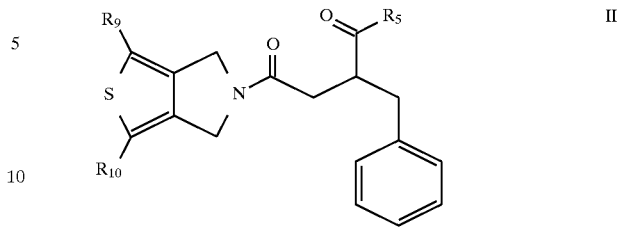

in which $R_5$ is as defined in claim 1 and $R_9$ and $R_{10}$, which are identical or different, represent a hydrogen atom, a halogen atom or a linear or branched alkyl group having from 1 to 4 carbon atoms.

5. Compound according to claim 1 exists in the form of a sodium or calcium salt.

6. Compound according to claim 1, which is γ-oxo-α(S)-(phenylmethyl)-2,3-dihydro-1H-isoindole-2-butanoic acid.

7. Compound according to claim 1, which is γ-oxo-α(R)-(phenylmethyl)-2,3-dihydro-1H-isoindole-2-butanoic acid.

8. Compound according to claim 1, which is γ-oxo-α(R,S)-(phenylmethyl)-2,3-dihydro-1H-isoindole-2-butanoic acid.

9. Compound according to claim 1, which is 5-fluoro-γ-oxo-α(S)-(phenylmethyl)-2,3-dihydro-1H-isoindole-2-butanoic acid.

10. Compound according to claim 1, which is 4-fluoro-γ-oxo-α(S)-(phenylmethyl)-2,3-dihydro-1H-isoindole-2-butanoic acid.

11. Compound according to claim 1, which is γ-oxo-α(S)-(phenylmethyl)-5,6-dihydro-4H-furo[3,4-c]pyrrole-5-butanoic acid.

12. Compound according to claim 1, which is γ-oxo-α(R,S)-(phenylmethyl)-5,6-dihydro-4H-furo[3,4-c]pyrrole-5-butanoic acid.

13. Compound according to claim 1 which is γ-oxo-α(S)-(phenylmethyl)-5,6-dihydro-4H-thieno[3,4-c]pyrrole-5-butanoic acid.

14. Compound according to claim 1, which is γ-oxo-α(R)-(phenylmethyl)-5,6-dihydro-4H-thieno[3,4-c]pyrrole-5-butanoic acid.

15. Compound according to claim 1, which is γ-oxo-α(R,S)-(phenylmethyl)-5,6-dihydro-4H-thieno[3,4-c]pyrrole-5-butanoic acid.

16. Compound according to claim 1, which is phenylmethyl γ-oxo-α(S)-(phenylmethyl)-5,6-dihydro-4H-thieno[3,4-c]pyrrole-5-butanoate.

17. Process for the preparation of the compound according to claim 1, comprising the following stages:

i) a compound of formula (III)

in which $R_1$, $R_2$, A and n are as defined in claim 1 is reacted with a compound of formula (IV)

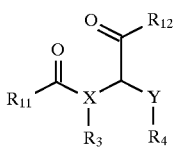

in which $R_3$, $R_4$, X and Y are as defined in claim 1, $R_{11}$ represents a halogen atom or a hydroxyl group and $R_{12}$ is a linear or branched alkoxy group having from 1 to 4 carbon atoms or a phenylalkoxy group in which the alkoxy part has from 1 to 4 carbon atoms so as to obtain a compound of formula (Ia)

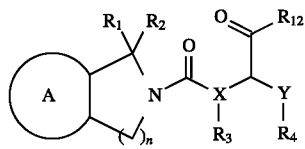

in which $R_1$, $R_2$, $R_3$, $R_4$, $R_{12}$, A, n, X and Y have the meanings given above, ii) hydrogenolyzing or hydrolyzing the $R_{12}$ group of the compound of formula (Ia) in order to prepare the compound of formula (I) where $r_5$ represents a hydroxyl group, iii) or to prepare the compounds of formula (I) where $R_5$ is either an $N_4$-methylpiperazinyl group, or a group $NHR_8$ where $R_8$ is a hydroxyl, pyridylmethyl or phenylmethyl group, reacting the compound of formula (Ia) with an amine of formula HZ in which Z represents an $N_4$-methylpiperazinyl group or a group $NHR_8$ as defined above, in the presence of carbonyldiimidazole.

18. Pharmaceutical composition comprising at least one compound according to claim 1 in combination with a pharmaceutically acceptable excipient.

19. Method for the treatment of diabetes, hyperglycaemia or obesity comprising administering to a person in need hereof an effective amount of a compound according to claim 1.

20. Method according to claim 19, wherein the compound is γ-oxo-α(S)-(phenylmethyl)-2,3-dihydro-1H-isoindole-2-butanoic acid or its sodium salt.

21. Method according to claim 19, wherein the compound is γ-oxo-α(R)-(phenylmethyl)-2,3-dihydro-1H-isoindole-2-butanoic acid or its sodium salt.

22. Method according to claim 19, wherein the compound is γ-oxo-α(R,S)-(phenylmethyl)-2,3-dihydro-1H-isoindole-2-butanoic acid or its sodium salt.

* * * * *